United States Patent
Li et al.

(10) Patent No.: US 12,306,166 B2
(45) Date of Patent: May 20, 2025

(54) SELF-ADAPTIVE OPTIMIZATION FRAMEWORK FOR WATER QUALITY PREDICTION

(71) Applicant: Hong Kong Applied Science and Technology Research Institute Company Limited, Hong Kong (CN)

(72) Inventors: Zheng Long Li, Hong Kong (CN); Laifa Fang, Shenzhen (CN)

(73) Assignee: Hong Kong Applied Science and Technology Research Institute Company Limited, Hong Kong (CN)

( * ) Notice: Subject to any disclaimer, the term of this patent is extended or adjusted under 35 U.S.C. 154(b) by 337 days.

(21) Appl. No.: 18/171,710

(22) Filed: Feb. 21, 2023

(65) Prior Publication Data
US 2024/0295539 A1     Sep. 5, 2024

(51) Int. Cl.
*G01N 33/18* (2006.01)

(52) U.S. Cl.
CPC .................... *G01N 33/18* (2013.01)

(58) Field of Classification Search
CPC ........... G01N 33/2847; G01N 33/2823; G01N 33/2852; G01N 27/221; G01N 27/223;
(Continued)

(56) References Cited

U.S. PATENT DOCUMENTS 6,536,272 B1 *  3/2003  Houston ............... G01N 1/12
                                              73/170.29
7,720,615 B2    5/2010  Kim
(Continued)

FOREIGN PATENT DOCUMENTS

CN  101916335 A  12/2010
CN  106056210 A  10/2016
(Continued)

OTHER PUBLICATIONS

A. M. Bakhach, E. P. K. Tsang, and V. L. R. Chinthalapatib, "TSFDC: A trading strategy based on forecasting directional change," Intelligent Systems in Accounting, Finance and Management 25, No. 3 (2018): 105-123.
(Continued)

*Primary Examiner* — Andre J Allen
(74) *Attorney, Agent, or Firm* — S&F/WEHRW

(57) ABSTRACT

The framework predicts water-quality data from observation data associated with raw features, e.g., rainfall. In the framework, an artificial neural network (ANN) computes the predicted water-quality data from feature data associated with impact features and derived from the observation data. The impact features are learnable, and are selected from impact-feature candidates comprising directional change-(DC-based) features each indicating occurrence of DC events in a corresponding raw feature. Including the DC-based features in the candidates enhances the ANN's ability of capturing significant change patterns of water quality due to extreme/unexpected events. The ANN architecture is also configurable according to model hyperparameters, which are learnable. The impact features and model hyperparameters are learnt by differential evolution for maximizing a prediction performance achieved by the ANN, thereby enabling the ANN architecture and impact features to be automatically optimized without requiring manual adjustment by domain experts in applying the ANN to different situations.

20 Claims, 8 Drawing Sheets

Self-Adaptive Optimization Framework

(58) Field of Classification Search
CPC ........... G01N 33/6893; G01N 33/1833; G01N
33/18; G01N 27/226; G01N 2800/52;
G01N 27/06; G01N 31/222; G01N
33/2835; G01N 33/28; G01N 22/00;
G01N 33/2829; G01N 33/48; G01N
33/6896; G01N 1/2035; G01N 21/3577;
G01N 33/14; G01N 33/2888; G01N
33/49; G01N 33/0011; G01N 33/146;
G01N 33/22; G01N 33/491; G01N 33/92;
G01N 21/359; G01N 24/08; G01N
27/121; G01N 2800/32; G01N 2800/50;
G01N 9/36; G01N 31/22; G01N 15/05;
G01N 2021/8416; G01N 2030/8813;
G01N 22/04; G01N 24/085; G01N 25/14;
G01N 27/07; G01N 2800/04; G01N
33/182; G01N 33/1826; G01N 33/24;
G01N 15/0618; G01N 19/10; G01N
27/225; G01N 27/3272; G01N 2800/347;
G01N 29/024; G01N 33/487; G01N
11/00; G01N 13/00; G01N 2013/006;
G01N 2015/092; G01N 21/33; G01N
21/65; G01N 2333/4712; G01N
2800/042; G01N 2800/60; G01N 30/02;
G01N 30/16; G01N 33/1886; G01N
33/492; G01N 33/6848; G01N 33/6887;
G01N 33/84; G01N 9/12; G01N 17/006;
G01N 2291/0256; G01N 2291/02818;
G01N 2291/02881; G01N 25/18; G01N
27/08; G01N 2800/044; G01N 29/036;
G01N 29/46; G01N 33/0047; G01N
33/2841; G01N 33/30; G01N 33/383;
G01N 1/18; G01N 1/4005; G01N 1/405;
G01N 11/14; G01N 13/02; G01N
15/0227; G01N 15/042; G01N
2013/0208; G01N 2030/025; G01N
2030/8827; G01N 21/3554; G01N 21/77;
G01N 21/78; G01N 2291/02809; G01N
2291/0422; G01N 2291/0426; G01N
2333/58; G01N 2333/705; G01N 25/56;
G01N 27/02; G01N 27/048; G01N
27/228; G01N 27/4168; G01N 2800/085;
G01N 2800/2821; G01N 29/022; G01N
29/14; G01N 29/326; G01N 30/00; G01N
30/18; G01N 30/34; G01N 30/82; G01N
30/8665; G01N 30/96; G01N 33/00;
G01N 33/0004; G01N 33/0006; G01N
33/0009; G01N 33/0026; G01N 33/0031;
G01N 33/03; G01N 33/2882; G01N
33/32; G01N 33/48785; G01N 33/48792;
G01N 33/493; G01N 33/4972; G01N
33/569; G01N 33/56966; G01N 33/574;
G01N 33/57407; G01N 33/57415; G01N
33/6863; G01N 33/743; G01N 33/86;
G01N 33/94; G01N 35/00594; G01N
35/00693; G01N 35/08; G01N 35/085;
G01N 9/02; G01N 9/26; G01N 1/40;
G01N 19/00; G01N 2030/8836; G01N
21/59; G01N 21/643; G01N 21/85; G01N
2291/02872; G01N 2291/0427; G01N
2333/4709; G01N 2405/04; G01N
27/026; G01N 2800/56; G01N 29/348;
G01N 31/16; G01N 33/0013; G01N
33/0029; G01N 33/005; G01N 33/04;
G01N 33/26; G01N 33/48707; G01N
33/50; G01N 33/5023; G01N 33/5091;
G01N 33/54373; G01N 33/66; G01N
33/6815; G01N 33/689; G01N 33/82;
G01N 5/045; G01N 1/02; G01N 1/28;
G01N 1/4022; G01N 1/4044; G01N
1/4055; G01N 11/02; G01N 11/167;
G01N 13/04; G01N 15/0205; G01N
15/0266; G01N 15/04; G01N 15/06;
G01N 15/0625; G01N 15/065; G01N
15/0656; G01N 15/08; G01N 15/1456;
G01N 15/1459; G01N 2001/2229; G01N
2001/244; G01N 2001/247; G01N
2001/2826; G01N 2001/2846; G01N
2001/4011; G01N 2001/4027; G01N
2001/4083; G01N 2011/0046; G01N
2011/0053; G01N 2011/008; G01N
2015/0288; G01N 2015/0294; G01N
2015/045; G01N 2015/0675; G01N
2015/0687; G01N 2015/1493; G01N
2021/3595; G01N 2021/6432; G01N
2021/773; G01N 2021/7783; G01N
2021/7786; G01N 2021/8411; G01N
2021/8557; G01N 2030/001; G01N
2030/009; G01N 2030/0095; G01N
2030/042; G01N 2030/062; G01N
2030/146; G01N 2030/201; G01N
2030/202; G01N 2030/207; G01N
2030/565; G01N 2030/765; G01N
2030/8822; G01N 2030/8831; G01N
2030/884; G01N 2030/8854; G01N
2030/8868; G01N 2035/00247; G01N
2035/00277; G01N 2035/00495; G01N
2035/0434; G01N 21/272; G01N 21/274;
G01N 21/31; G01N 21/41; G01N 21/43;
G01N 21/53; G01N 21/532; G01N
21/553; G01N 21/6428; G01N 21/7703;
G01N 21/82; G01N 21/9018; G01N
21/9081; G01N 22/02; G01N
2201/06113; G01N 2201/1211; G01N
2203/0025; G01N 2223/056; G01N
2291/011; G01N 2291/015; G01N
2291/0215; G01N 2291/0222; G01N
2291/0224; G01N 2291/02433; G01N
2291/02491; G01N 2291/0255; G01N
2291/02836; G01N 2291/02845; G01N
2291/0421; G01N 2291/0423; G01N
2291/045; G01N 2333/4716; G01N
2333/495; G01N 2333/5412; G01N
2333/5421; G01N 2333/75; G01N
2333/765; G01N 2333/805; G01N
2333/924; G01N 24/081; G01N 2405/06;
G01N 2405/08; G01N 25/02; G01N
25/142; G01N 25/16; G01N 25/60; G01N
25/62; G01N 25/70; G01N 2500/04;
G01N 2570/00; G01N 27/025; G01N
27/123; G01N 27/126; G01N 27/127;
G01N 27/18; G01N 27/302; G01N
27/327; G01N 27/414; G01N 27/4146;
G01N 27/423; G01N 27/44791; G01N
27/48; G01N 27/49; G01N 2800/02;
G01N 2800/06; G01N 2800/062; G01N
2800/102; G01N 2800/104; G01N
2800/164; G01N 2800/22; G01N
2800/24; G01N 2800/2814; G01N
2800/2835; G01N 2800/2871; G01N 2800/30; G01N 2800/301; G01N 2800/302; G01N 2800/321; G01N 2800/322; G01N 2800/323; G01N 2800/325; G01N 2800/367; G01N 2800/40; G01N 2800/7009; G01N 2800/7042; G01N 2800/7095; G01N 29/028; G01N 29/22; G01N 29/222; G01N 29/30; G01N 29/4427; G01N 30/0005; G01N 30/06; G01N 30/08; G01N 30/12; G01N 30/14; G01N 30/20; G01N 30/24; G01N 30/463; G01N 30/56; G01N 30/7206; G01N 30/7233; G01N 30/76; G01N 30/8603; G01N 30/8658; G01N 30/8675; G01N 30/8679; G01N 30/8686; G01N 30/88; G01N 30/90; G01N 33/0014; G01N 33/0037; G01N 33/004; G01N 33/02; G01N 33/15; G01N 33/1846; G01N 33/1853; G01N 33/225; G01N 33/2805; G01N 33/2811; G01N 33/343; G01N 33/36; G01N 33/365; G01N 33/442; G01N 33/48721; G01N 33/497; G01N 33/5005; G01N 33/5038; G01N 33/5088; G01N 33/52; G01N 33/53; G01N 33/536; G01N 33/5375; G01N 33/564; G01N 33/56972; G01N 33/573; G01N 33/57423; G01N 33/57438; G01N 33/57488; G01N 33/585; G01N 33/68; G01N 33/6806; G01N 33/6854; G01N 33/6872; G01N 33/721; G01N 33/74; G01N 33/9453; G01N 35/00; G01N 35/00069; G01N 35/00603; G01N 35/00663; G01N 35/10; G01N 35/1095; G01N 35/1097; G01N 5/025; G01N 7/00; G01N 7/14; G01N 9/002; G01N 9/04; G01N 9/14; G01N 9/24; G01N 9/32; G01N 1/2214; G01N 2021/154; G01N 2030/185; G01N 2030/528; G01N 2035/00158; G01N 2035/1055; G01N 21/658; G01N 21/81; G01N 2291/014; G01N 2291/02408; G01N 2291/02416; G01N 2291/02425; G01N 2291/02466; G01N 2291/106; G01N 2291/2695; G01N 333/4745; G01N 2333/65; G01N 2333/78; G01N 2333/80; G01N 2474/20; G01N 25/08; G01N 27/3274; G01N 2800/329; G01N 29/02; G01N 29/28; G01N 30/72; G01N 31/223; G01N 33/0081; G01N 33/1893; G01N 33/205; G01N 33/38; G01N 33/46; G01N 33/4875; G01N 33/48757; G01N 33/48778; G01N 33/5008; G01N 33/5029; G01N 33/5044; G01N 33/5308; G01N 33/542; G01N 33/54388; G01N 33/558; G01N 33/587; G01N 33/6812; G01N 33/6884; G01N 35/1016; G01N 9/00

USPC .......................................................... 73/61.43

See application file for complete search history.

(56) References Cited

U.S. PATENT DOCUMENTS

| | | | |
|---|---|---|---|
| 8,510,242 | B2 | 8/2013 | Al-Fattah |
| 2025/0020581 | A1* | 1/2025 | Milligan ................ G01N 33/18 |

FOREIGN PATENT DOCUMENTS

| | | | | |
|---|---|---|---|---|
| CN | 107239852 | A | | 10/2017 |
| CN | 107292383 | A | | 10/2017 |
| CN | 111291937 | A | | 6/2020 |
| CN | 111915097 | A | | 11/2020 |
| CN | 113033861 | A | | 6/2021 |
| CN | 113297788 | A | | 8/2021 |
| CN | 114154583 | A | | 3/2022 |
| CN | 114896885 | A | | 8/2022 |
| CN | 118518842 | A | * | 8/2024 |
| CN | 118735050 | A | * | 10/2024 |
| IN | 202341036638 | A | * | 6/2023 |
| KR | 20220105530 | A | | 7/2022 |
| KR | 20220164271 | A | * | 10/2024 |
| KR | 20240143018 | A | * | 10/2024 |
| KR | 102764329 | B1 | * | 2/2025 |

OTHER PUBLICATIONS

R. Storn and K. Price, "Differential evolution—a simple and efficient heuristic for global optimization over continuous spaces," Journal of Global Optimization 11: 341-359, 1997, pp. 341-359.

* cited by examiner

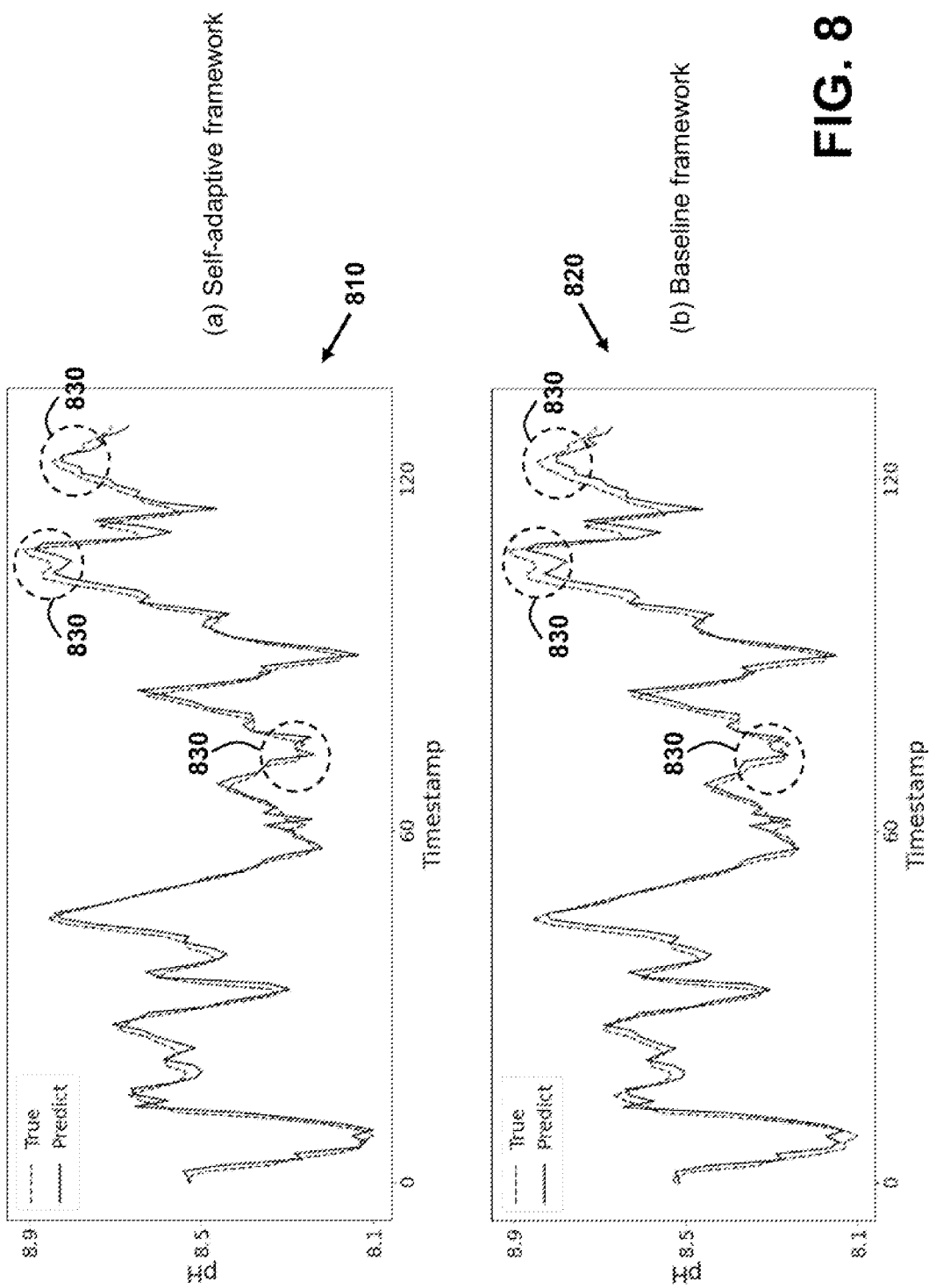

SELF-ADAPTIVE OPTIMIZATION FRAMEWORK FOR WATER QUALITY PREDICTION

LIST OF ABBREVIATIONS

ANN artificial neural network
DE differential evolution
GA genetic algorithm
GRU gate recurrent unit
LSTM long short-term memory
MLP multilayer perceptron
SODE self-adaptive optimization differential evolution
TS time series

TECHNICAL FIELD

The present disclosure relates to a self-adaptive optimization framework for machine-learning prediction of water quality. The framework automatically optimizes an architecture of ANN and determines a plurality of impact features relevant to water quality prediction as an input to the ANN without a need for manual adjustment by domain experts in applying the ANN to different situations or geographical regions of water-quality prediction. The framework also proposes using DC-based features in enhancing the ANN's ability of capturing possible significant change patterns of water quality due to extreme or unexpected events.

BACKGROUND

With the rapid development of industries, protecting the environment has been a very challenging task due to industrial pollution in recent years. Water quality is one of the essential components of urban development that directly affects human health. To better maintain the quality of water, not only do the water data need to be monitored in real time, but also the future trend of water quality is required to be forecasted so that special treatments to possible pollutants and cycle fluctuations can be prepared in advance.

Prediction of future water quality based on present and past water-quality-related observation data is therefore of practical importance to people's life in the society. There are many factors affecting water quality, e.g., climatic factors such as rainfall and temperature, chemical factors such as nitrogen and phosphorous contents in a catchwater area due to agricultural waste contamination, biological factors such as Fecal Coliform Group concentration, location factors such as water sources being in lakes, rivers, estuaries, etc., and environmental factors such as occurrence of sudden spillage of industrial sewage into a fresh water source. Since many factors of vastly different nature are involved in controlling water quality with different degrees of impact, it is attractive to use machine-learning techniques in predicting water quality. Of relevance to the present disclosure, there are two technical problems associated with using the machine-learning techniques, in particular using ANN models, in predicting water quality.

It is first noticed that the observation data relevant to water quality prediction and used for training a machine-learning model are mostly given as a TS of data. The TS is a data sequence with data samples taken with a certain sampling interval. Usually, the sampling interval is long, e.g., in the order of hours or even days, due to various reasons. In addition, the TS data are usually prepared from raw measurement data with downsampling. The sampling interval used in the TS is usually determined by domain experts based on domain knowledge and practical constraints. For instance, some observation variables are believed to be slowly varying so that a high sampling rate is not necessary; and/or a high cost of training the machine-learning model is resulted in case of a high sampling rate. In case a sudden extreme or unexpected event occurs for a short time, the TS often misses the occurrence of such event since the sampling rate of the TS is not high enough. However, increasing the sampling rate is a costly approach at least in training the machine-learning model. Hence, the first technical problem to be tackled is how to extract information on the extreme or unexpected event from the observation data without resorting to increasing the sampling rate.

It is desirable to use a machine-learning technique to predict water quality under different situations or for different geographical regions. It requires optimization of the machine-learning model architecture and optimized selection of impact factors (or impact features) that are determining factors of water quality prediction among a set of impact-feature candidates. In the art, however, the ANN architecture and the impact features are most-often manually adjusted by domain experts with trial-and-error schemes to avoid introducing irrelevant noise features. Hence, the underlying machine-learning model for water quality prediction needs to be redesigned when applied to different situations or other geographical areas for accurate prediction. In the present disclosure, the second technical problem to be tackled is how to automatically optimize the ANN architecture and select an optimized set of impact features without a need for manual adjustment.

In the art, using machine-learning techniques for forecasting useful indicators, such as water quality, electricity consumption and air quality, based on TS data in complex settings have been addressed in, e.g., CN 101916335A, CN 107292383A, CN 107239852A, CN 106056210A and U.S. Pat. No. 7,720,615 B2. In these references, the ANN models therein process the observation data on a TS view only, and do not address how to identify or detect extreme or unexpected events that occur in a short time. Furthermore, architectures and hyperparameters of these ANN models for prediction are default values or are decided by empirical observations. These model settings may not fit other scenarios or datasets, and the ANN models are required to be redesigned manually for other applications. U.S. Pat. No. 8,510,242 B2 discloses an ANN model for determining relative permeability of hydrocarbon reservoirs. In addition, the architecture of the ANN model is optimized by using a GA. The GA is a conventional meta-heuristic algorithm that has fixed mutation strategies and controlling parameters. The ANN model used for one application may not be appropriate for use in different applications.

There is a need in the art for an improved machine-learning technique addressing the above-mentioned two problems in predicting water quality.

SUMMARY

Disclosed herein is a computer-implemented method for predicting water quality from observation data associated with a plurality of raw features relevant to water-quality prediction to thereby generate predicted water-quality data.

The method comprises setting up an ANN for computing the predicted water-quality data from feature data associated with a plurality of impact features. The feature data associated with the plurality of impact features are computed from the observation data. The plurality of impact features is learnable. An architecture of the ANN is configurable according to a plurality of model hyperparameters. The ANN has a plurality of ANN model parameters for configuring an input-output relationship of the ANN. The method further comprises learning the plurality of impact features, the plurality of model hyperparameters and the plurality of ANN model parameters.

In the present disclosure, certain embodiments of the disclosed method provide a technical advantage of enhancing the ability of the ANN in capturing possible significant change patterns of water quality due to extreme or unexpected events. Particularly, in learning the plurality of impact features, an individual impact feature is selected from a plurality of impact-feature candidates comprising a plurality of DC-based features. An individual DC-based feature is associated with a corresponding raw feature and is used to indicate occurrence of any DC event in the corresponding raw feature. An inclusion of the individual DC-based feature in the plurality of impact-feature candidates enhances the ANN's ability of capturing possible significant change patterns of water quality due to extreme or unexpected events.

The individual DC-based feature is further associated with a DC threshold for controlling detection of any DC event in the corresponding raw feature. In certain embodiments, plural respective DC-based features associated with a same corresponding raw feature are associated with different DC thresholds for enabling the ANN to more effectively learn to distinguish extreme or unexpected events of different degrees of severity.

In certain embodiments, the plurality of impact-feature candidates further comprises a plurality of downsampled raw features. In addition, the individual DC-based feature is further associated with a corresponding downsampled raw feature. Feature data associated with the corresponding downsampled raw feature are obtained by downsampling respective observation data associated with the corresponding raw feature.

In certain embodiments, the corresponding raw feature is excluded from the plurality of impact-feature candidates such that an inclusion of the individual DC-based feature and the corresponding downsampled raw feature into the plurality of impact-feature candidates enhances the ANN's ability of capturing possible significant change patterns of water quality due to extreme or unexpected events while avoiding the ANN from directly processing feature data associated with the corresponding raw feature.

In the present disclosure, certain embodiments of the disclosed method provide a technical advantage of avoiding a need to manually adjust or manually tune the ANN architecture and the plurality of impact features in applying the disclosed method to different situations of water-quality prediction. Particularly, the plurality of impact features and the plurality of model hyperparameters are learnt by DE for maximizing a water-quality prediction performance achieved by the ANN. As a result, it enables the ANN architecture and the plurality of impact features to be automatically optimized without a need for manual adjustment by domain experts in applying the ANN to different situations of water-quality prediction.

Preferably, the learning of the plurality of impact features, the plurality of model hyperparameters and the plurality of ANN model parameters comprises: obtaining a training dataset for training the ANN, and a testing dataset for verifying the trained ANN; setting up a search space for suggesting different impact-feature candidates and different model-hyperparameter options such that the plurality of impact-feature candidates and a plurality of model-hyperparameter options are obtainable from the search space, wherein the plurality of model hyperparameters is selected from the plurality of model-hyperparameter options; and performing an iterative process. Furthermore, an individual iteration of the iterative process comprises: generating a suggestion on both of the plurality of impact features and the plurality of model hyperparameters, wherein if said individual iteration is an initial iteration, the suggestion is initialized with a preset suggestion or is randomly generated in the search space, else the suggestion is generated by performing DE-based operations of mutation, crossover and selection in the search space after mutation strategies and control parameters of the three DE-based operations are adapted according to historical performance of water-quality prediction due to suggestions made in past iterations; configuring the architecture and input-output relationship of the ANN according to the suggestion; after the architecture and input-output relationship of the ANN are configured, learning the plurality of ANN model parameters by training the ANN according to data in the training dataset, whereby the trained ANN is obtained; verifying a prediction accuracy of the trained ANN according to data in the testing dataset to thereby yield a prediction-performance value; and if the prediction-performance value converges or a predefined stopping criterion is met, then terminating the iterative process such that the trained ANN as obtained in said individual iteration is usable for inference, else proceeding to execute a next iteration.

Preferably, the mutation strategies and control parameters are adapted by a mutation-strategy adaption mechanism and a control-parameter adaption mechanism, respectively, for enhancing an efficiency in searching for the suggestion across different situations of water-quality prediction. In the mutation-strategy adaption mechanism, the mutation strategies are adapted by adjusting selection probabilities of each mutation strategy according to historical ranking-based performance among the mutation strategies. In the control-parameter adaption mechanism, the control parameters are adapted by respectively adjusting the control parameters to weighted successful control parameters obtained in the past iterations.

Preferably, said individual iteration of the iterative process further comprises decoding the generated suggestion into the plurality of impact features and the plurality of model hyperparameters by a decoding algorithm such that the plurality of impact features and the plurality of model hyperparameters as decoded are interpretable by the ANN. The decoding algorithm is configured with a plurality of transformation rules respectively used for processing data of a plurality of data types, and wherein the plurality of data types includes binary data type, category data type, integer data type and real number data type.

In certain embodiments, the method further comprises: setting up a data augmentation module for computing the feature data associated with the plurality of impact features from the observation data, whereby a water-quality prediction model for computing the predicted water-quality data from the observation data is formed by a cascade of the data augmentation module and the ANN; and setting up a SODE controller for learning the plurality of impact features and the plurality of model hyperparameters. The SODE controller is communicable with the water-quality prediction model. Furthermore, the SODE controller is arranged to: perform the iterative process; during execution of said individual iteration, send the plurality of model hyperparameters and the plurality of impact features as decoded to the ANN and the data augmentation module, respectively, so as to configure the ANN architecture and to inform the data augmentation module to calculate the feature data associated with the plurality of impact features; during execution of said individual iteration, train the ANN by commanding the data augmentation module to process the observation data recorded in the training dataset, and by commanding the ANN to send the predicted water-quality data as obtained to the SODE controller; and during execution of said individual iteration, verify the prediction accuracy of the trained ANN by commanding the data augmentation model to process the observation data recorded in the testing dataset, and by commanding the ANN to send the predicted water-quality data as obtained to the SODE controller.

In certain embodiments, the plurality of model hyperparameters is arranged to provide information at least on type and size of the ANN to the ANN. The plurality of model-hyperparameter options includes different combinations of the ANN type and the ANN size. The ANN type used in generating the different combinations may be selected from a MLP, a LSTM and a GRU.

In certain embodiments, the ANN is a modular neural network comprising a plurality of learning submodules and a dense layer. The plurality of learning submodules is used for processing the feature data associated with the plurality of impact features. An individual learning submodule is realized as a standalone neural network for processing feature data associated with a corresponding impact feature selected from the plurality of impact features to thereby yield feature data of a middle feature. The dense layer is used for fusing feature data of respective middle features to generate the predicted water-quality data. The individual learning submodule may be realized by a MLP, a LSTM or a GRU.

In certain embodiments, the method further comprises: after the architecture and input-output relationship of the ANN are configured by the learnt plurality of model hyperparameters and the learnt plurality of the ANN model parameters, respectively, inferring the predicted water-quality data from the observation data by computing the feature data associated with the learnt plurality of impact features from the observation data and then using the ANN to compute the predicted water-quality data from the computed feature data associated with the learnt plurality of impact features.

Other aspects of the present disclosure are disclosed as illustrated by the embodiments hereinafter.

BRIEF DESCRIPTION OF THE DRAWINGS

FIG. 8 plots actually-measured pH values and predicted ones as obtained in an experiment conducted for the proposed self-adaptive water quality prediction framework and a baseline framework, demonstrating the superior water-quality prediction performance offered by the proposed framework over the baseline framework in the presence of extreme or unexpected events.

Figure 1:
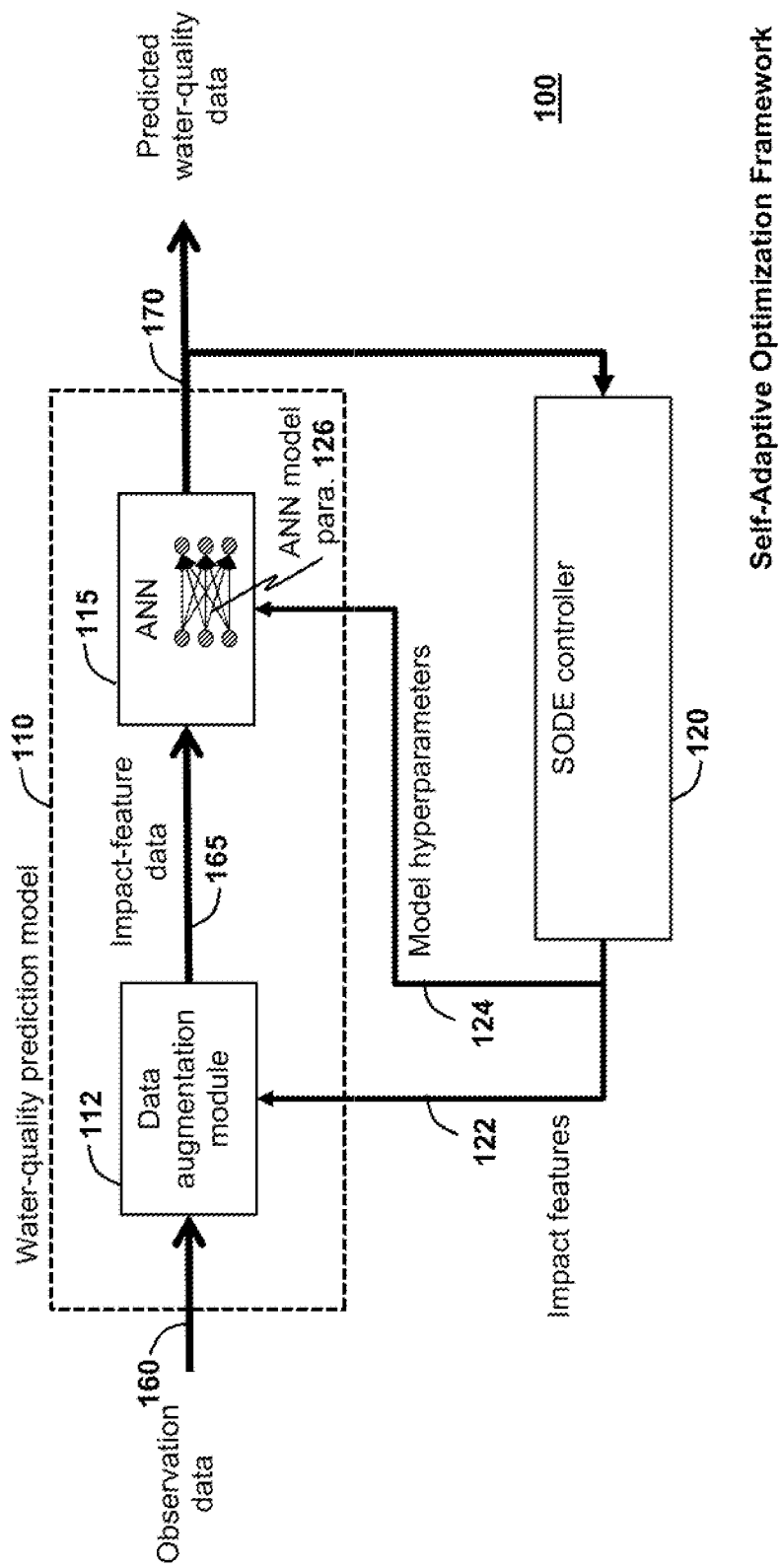
FIG. 1 depicts a schematic diagram of a self-adaptive water quality prediction framework, where the framework has a water-quality prediction model and a SODE controller, and the prediction model is formed by a cascade of a data augmentation module and an ANN. A computer-implemented method as disclosed herein for predicting water quality based on machine learning is developed based on the framework.

Skilled artisans will appreciate that elements in the figures are illustrated for simplicity and clarity and have not necessarily been depicted to scale.

DETAILED DESCRIPTION

As used herein, "observation data" are data generated, directly or indirectly, from measuring one or more observation variables. In water quality measurement, a single observation variable may be a climatic indicator (rainfall, temperature, etc.), a chemical indicator (nitrogen content, phosphor content, etc.), a biological indicator (bacteria concentration, etc.), a water-source location, etc. The observation data of an observation variable in water-quality measurement may be primary data obtained by directly measuring the observation variable, or may be secondary data obtained from processing the primary data.

As used herein, "raw observation data", or "raw data" in short, are observation data that are primary data.

As used herein, "a TS" is a sequence of data, where plural data in the sequence are obtained at different time instants. The data in the TS may be primary data or secondary data. The different time instants may have a fixed time interval such that the data are obtained at a certain sampling rate. Alternatively, it is also possible that the different time instants are not evenly distributed over time.

Of relevance to the present disclosure, a first TS of raw observation data is often used to derive a second TS of observation data by downsampling the first TS, where the second TS is to be used in predicting water quality. The downsampling may be a decimation operation, an operation of low-pass filtering the first TS followed by decimation, etc. Note that the first TS has a sampling rate higher than that of the second TS. For instance, the first TS of raw observation data is obtained by making minute-based measurements while the second TS of observation data are sampled every 5 minutes, every hour, every 6 hours, or every day, etc.

The present disclosure proposes a self-adaptive water quality prediction framework. Main components of the framework include a deep learning-based water-quality prediction model and a heuristic-based self-adaptive optimization controller. The water-quality prediction model learns underlying patterns from selected impact features (e.g., rainfall, nitrogen content, and location of the water source), and then forecasts the future trend of water quality (e.g., pH, turbidity, etc.). According to the performance of the prediction model, the self-adaptive optimization controller automatically optimizes an ANN architecture of the prediction model and a list of impact features. New suggestions generated by the controller are further fed to the prediction model for evaluation. The framework is recursively updated until certain stopping criteria are met, and finally outputs the optimal ANN settings and impact features with the optimal prediction performance.

The present disclosure provides a computer-implemented method for predicting water quality from observation data associated with a plurality of raw features relevant to water-quality prediction to thereby generate predicted water-quality data. The disclosed method is a machine-learning method, and the observation data are relevant to water-quality prediction. The disclosed method is developed based on the self-adaptive water quality prediction framework. Note that the framework is an implementation of a certain embodiment of the disclosed method in software. It is intended that the present disclosure encompasses all embodiments of the disclosed method.

Figure 2:
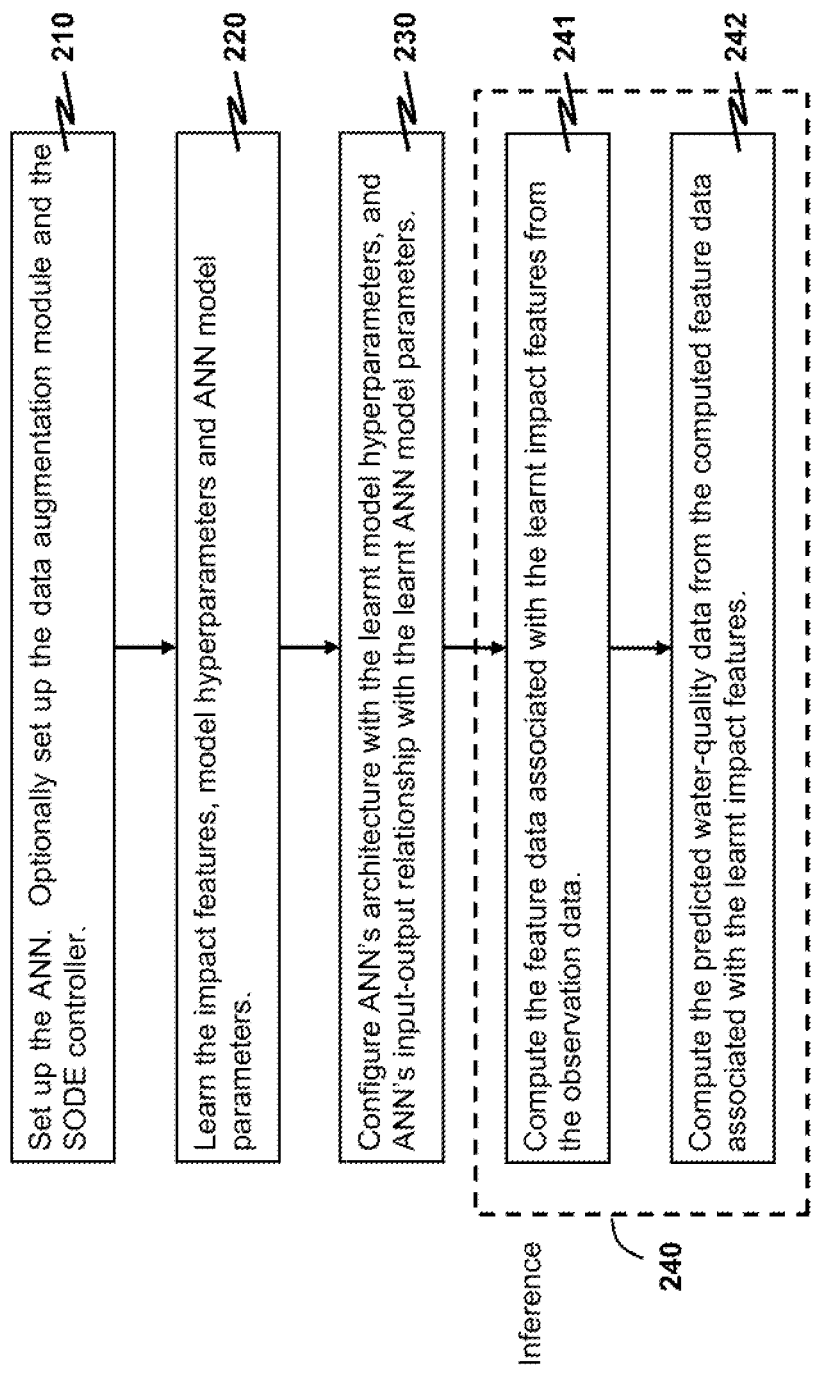
FIG. 2 depicts a flowchart showing exemplary steps of the disclosed method.

The disclosed method is illustrated as follows with the aid of FIGS. 1 and 2. FIG. 1 depicts a schematic diagram of the self-adaptive water quality prediction framework (referenced as 100). FIG. 2 depicts a flowchart showing typical steps of the disclosed method.

Refer to FIG. 1. The framework 100 comprises a water-quality prediction model 110 and a SODE controller 120.

The water-quality prediction model 110 is used for computing predicted water-quality data 170 from observation data 160 relevant to water-quality prediction. Typically, the predicted water-quality data 170 are future water-quality predictions and the observation data 160 are present and/or past measurement data of impact factors that influence water quality. The observation data 160 are associated with the plurality of raw features, where each raw feature is one of these impact factors. For instance, a raw feature may be selected from the climatic factors, chemical factors, biological factors, location factors and environmental factors as elaborated above. The prediction model 110 is formed as a cascade of a data augmentation module 112 and an ANN 115. The ANN 115 is used for computing the predicted water-quality data 170 from feature data 165 associated with a plurality of impact features 122. The ANN 115 is preferred to be a deep-learning model. The feature data 165 are calculated from the observation data 160 by the data augmentation module 112 according to the plurality of impact features 122. Furthermore, the plurality of impact features 122 is learnable, with a goal that an optimal set of impact features is used by the prediction model 110 to yield the best prediction performance. An architecture of the ANN 115 is configurable according to a plurality of model hyperparameters 124. Examples of the model hyperparameters 124 are the topology, size, types of different layers, types of activation functions, etc. of the ANN 115. In addition, the ANN 115 has a plurality of ANN model parameters 126 for configuring an input-output relationship of the ANN 115. An example of the ANN model parameters 126 is a set of node weights if the ANN 115 is implemented as a MLP neural network.

The SODE controller 120 is proposed to automatically optimize feature-related and model-related parameters in terms of the performance of the water-quality prediction model 110. In addition, the SODE controller 120 is a domain-mixed optimizer handling water-quality impact factors at different data types. Note that the framework 100 is "self-adaptive" in that the SODE controller 120 provides automatic optimization of the feature- and model-related parameters without manual intervention.

Specifically, the SODE controller 120 is used for learning the plurality of impact features 122 and the plurality of model hyperparameters 124 based on a DE technique. The DE technique uses a meta-heuristic algorithm to do the learning. The SODE controller 120 is communicable with the water-quality prediction model 110, and supplies the learnt plurality of impact features 122 and the learnt plurality of model hyperparameters 124 to the data augmentation module 112 and the ANN 115, respectively. The learnt plurality of impact features 122 is used to configure the data augmentation module 112 in computing the impact-feature data 165. The learnt plurality of model hyperparameters 124 is used to configure the architecture of ANN 115.

Refer to FIG. 2. The disclosed method comprises steps 210, 220, 230 and 240.

In the step 210, the ANN 115 is set up. As the disclosed method is a computer-implemented method, setting up the ANN 115 means providing a software realization of the ANN 115 with desired properties as taught herein in one or more computers or in any computing device.

After the ANN 115 is set up, the plurality of impact features 122, the plurality of model hyperparameters 124 and the plurality of ANN model parameters 126 are learnt in the step 220. Generally, the learning of the plurality of impact features 122, the plurality of model hyperparameters 124 and the plurality of ANN model parameters 126 is a training process based on historical records of actual (not predicted) water-quality data and measurement data of impact factors that influence water quality over a long period of time. The plurality of impact features 122, the plurality of model hyperparameters 124 and the plurality of ANN model parameters 126 are usually optimized in a sense of maximizing a performance or accuracy of water-quality prediction.

After the step 220 is performed, the architecture and input-output relationship of the ANN 115 are configured by the learnt plurality of model hyperparameters 124 and the learnt plurality of the ANN model parameters 126, respectively, in the step 230. As a result, the ANN 115 is trained.

After the ANN 115 is trained, the predicted water-quality data 170 can be inferred from the observation data 160 in the step 240. Specifically, the step 240 is accomplished by computing the feature data 165 associated with the learnt plurality of impact features 122 from the observation data 160 (step 241) and then using the ANN 115 to compute the predicted water-quality data 170 from the computed feature data 165 (step 242). The computation of the impact-feature data 165 from the observation data 160 may be accomplished by the data augmentation module 112, or may be done in other computing modules.

The first technical problem as mentioned above regarding how to extract information of an extreme or unexpected event from the observation data 160 in TS form by using machine learning is addressed as follows. Particularly, the concept of DC, which is used in the field of financial-trading decision making and which is seldom considered in the field of water-quality prediction, is advantageously utilized with machine learning to solve the first technical problem. For information on the DC concept, see A. M. BAKHACH, E. P. K. TSANG and V. L. R. CHINTHALAPATI, "TSFDC: A trading strategy based on forecasting directional change," *Intelligent Systems in Accounting, Finance and Management*, 25, no. 3 (2018): 105-123, the disclosure of which is incorporated by reference herein.

Figure 3:
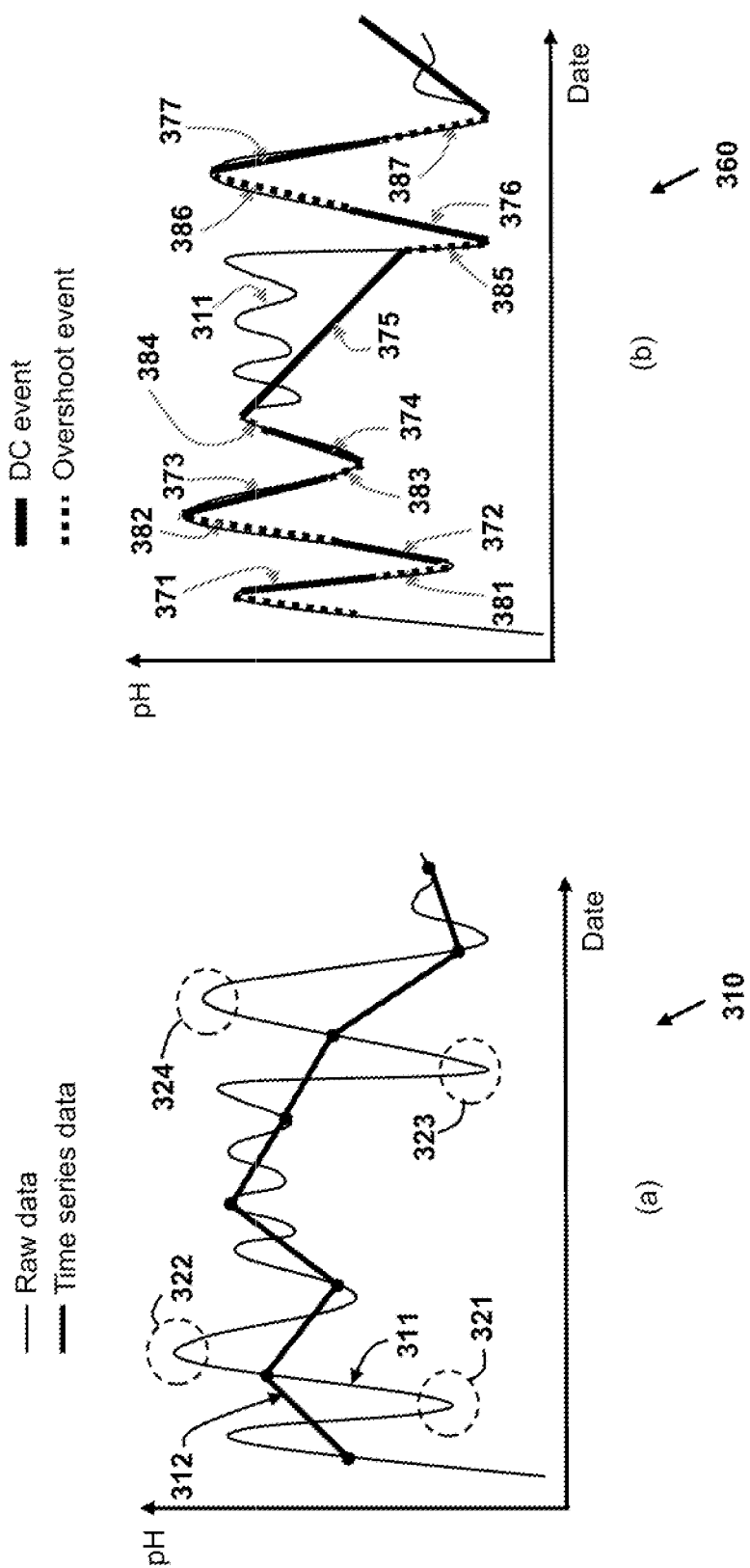
FIG. 3 provides a comparison in detecting occurrence of extreme or unexpected events between using sampled data in a TS and using DC events identified under a DC framework.

FIG. 3 provides a comparison in detecting occurrence of extreme or unexpected events between using sampled data in a TS and using identified DC events.

Subplot (a) 310 plots raw observation data 311 and corresponding sampled data 312 in the TS over time, where the sampled data 312 are obtained by downsampling the raw observation data 311. As mentioned above, the sampling interval used in the sampled data 312 is usually decided by domain experts based on domain knowledge and practical constraints in water-quality prediction. From the subplot (a) 310, it is apparent that short-time extreme/unexpected events 321-324 are not identifiable since the time interval between successive samples (i.e. the sampling interval) in the TS is too large, and is larger than the occurrence duration of each short-time extreme/unexpected event. Some significant change information between the successive samples is probably missed during sampling. There may be some potentially extreme or unexpected events (such as industrial sewage leakage) that may cause significant changes of water quality within a short period of time in which conventional deep-learning ANN models configured to use TS data 312 probably fail at predicting unusual events and changes. It is also demonstrated that if the raw data 311 instead of the TS data 312 are processed by a machine-learning model, the two extreme/unexpected events 322, 323, for example, may be identifiable but the machine-learning model is also required to distinguish these two extreme/unexpected events 322, 323 from other less-serious spurious peaks in between the two extreme/unexpected events 322, 323. Training and inference costs of the machine-learning model are inevitably increased. More training data are required to train the ANN 115 for maintaining a certain prediction performance. In case the body of training data is not large enough, it results in a degradation of prediction performance.

Identifying directional changes in the raw observation data 311 enables identification of extreme/unexpected events without increasing the sampling rate of the TS data 312. In the framework of DC, the sequence of raw data 311 is viewed as a sequence of alternating uptrends and downtrends. A change in magnitude of the raw data 311 during an uptrend or a downtrend is at least equal to a DC threshold. The DC threshold is selected to be a value that is considered substantial by those skilled in the art, e.g., 1%, 5% and 10%. Different values may be set for the DC threshold, resulting in identifying DC events of different degrees in severity, significance, nature, etc. In the DC framework, a change from uptrend to downtrend or vice versa marks an occurrence of a DC event. Specifically, the change in magnitude of the raw data 311 during the DC event is equal to the size specified by the DC threshold. The uptrend or downtrend usually continues beyond the duration of the DC event by having a further change in magnitude beyond the size specified by the DC threshold, resulting in an overshoot event.

Subplot (b) 360 plots the raw observation data 311 and a collection of DC events 371-377 and overshoot events 381-387. In the subplot (b) 360, a DC threshold of 5% is used as an example for detecting the DC events 371-377 from the raw data 311. With a knowledge of the DC events 371-377, the short-time extreme/unexpected events 321-324 can be more easily captured by the machine-learning model. Table 1 lists the DC events (uptrend or downtrend) identified from the raw data 311 under different DC threshold values of 1%, 5% and 10%.

TABLE 1

| DC threshold | $t_0$ | $t_1$ | ... | $t_{T-1}$ | $t_T$ |
|---|---|---|---|---|---|
| 1% | Up | Down | ... | Up | Down |
| 5% | Up | Up | ... | Up | Down |
| 10% | Down | Down | ... | Up | Down |

(Date)

Table 1 shows that by using different DC threshold values, different patterns of DC events are obtained. The different patterns are useful for distinguishing extreme/unexpected events of different types, e.g., accidental spillage of industrial/agricultural/upstream sewage of different scales. Note that each DC event is related to an occurrence of a directional change that is locally occurred at a given time instant rather than related to a trend of the entire sequence of the raw observation data 311. Thus, data points on DC event data are not sampled at a fixed interval, and only the data points representing significant changes are recorded, namely, the data points at time instants $t_0, t_1, \ldots, t_{T-1}, t_T$.

The DC framework is applied to the disclosed method by the following arrangement.

In learning the plurality of impact features in the step 220, an individual impact feature is selected from a plurality of impact-feature candidates. Advantageously, the plurality of impact-feature candidates comprises a plurality of DC-based features, where an individual DC-based feature is associated with a corresponding raw feature and is used to indicate occurrence of any DC event in the corresponding raw feature. The corresponding raw feature is selected from the plurality of raw features. Advantageously, an inclusion of the individual DC-based feature in the plurality of impact-feature candidates enhances the ability of the ANN 115 in capturing possible significant change patterns of water quality due to extreme or unexpected events.

Note that a DC event indicated in the individual DC-based feature is either an uptrend event or a downtrend event. Also note that the individual DC-based feature is further associated with a DC threshold for controlling detection of any DC event in the corresponding raw feature.

Preferably, plural respective DC-based features associated with a same corresponding raw feature are associated with different DC thresholds for enabling the ANN 115 to more effectively learn to distinguish extreme or unexpected events of different degrees of severity.

The corresponding raw feature may or may not be included in the plurality of impact-feature candidates as a candidate for selection to be an impact feature adopted by the water-quality prediction model 110. On the other hand, it is advantageous to allow a downsampled raw feature to be a candidate in impact-feature selection, where the downsampled raw feature has a lower sampling rate in TS data than a corresponding original raw feature. As analyzed above, using the downsampled raw feature instead of the corresponding original one reduces the training and inference costs.

Preferably, the plurality of impact-feature candidates further comprises a plurality of downsampled raw features. In particular, the individual DC-based feature is further associated with a corresponding downsampled raw feature, which is selected from the plurality of downsampled raw features. Feature data associated with the corresponding downsampled raw feature are obtained by downsampling respective observation data associated with the corresponding raw feature.

In certain embodiments, the corresponding raw feature is excluded from the plurality of impact-feature candidates. As a result, an inclusion of the individual DC-based feature and the corresponding downsampled raw feature into the plurality of impact-feature candidates enhances the ability of the ANN 115 in capturing possible significant change patterns of water quality due to extreme or unexpected events while avoiding the ANN 115 from directly processing feature data associated with the corresponding raw feature.

The second technical problem as mentioned above regarding how to automatically optimize the ANN architecture and select an optimized set of impact features without a need for manual adjustment is addressed as follows. In particular, the ANN architecture and the plurality of impact features are optimized by using DE, which is an evolutionary computation technique, to learn the plurality of model hyperparameters and the plurality of impact features. For information on the DE, see R. STORN and K. PRICE, "Differential evolution—a simple and efficient heuristic for global optimization over continuous spaces," *Journal of Global Optimization* 11: 341-359, 1997, pp. 341-359, the disclosure of which is incorporated by reference herein.

DE was proposed by R. STORN and K. PRICE and is frequently used to solve complex optimization problems. DE is a population-based method. It generates new offspring by recombining solutions under certain conditions. The current individual solution is replaced if it is outperformed by the new offspring solution. DE is considered robust and simple because its search process is governed by few algorithm-specific parameters, such as scaling factor and crossover rate. DE produces new offspring solutions through three mechanisms, namely, mutation, crossover and selection. Mutation and crossover are commonly observed to have a greater impact on the algorithm's search performance.

In the step 220 of the disclosed method, the plurality of impact features 122 and the plurality of model hyperparameters 124 are learnt by DE for maximizing a water-quality prediction performance achieved by the ANN 115, thereby enabling the architecture of ANN 115 and the plurality of impact features to be automatically optimized without a need for manual adjustment or manual tuning by domain experts in applying the ANN 115 to different situations of water-quality prediction.

Figure 4:
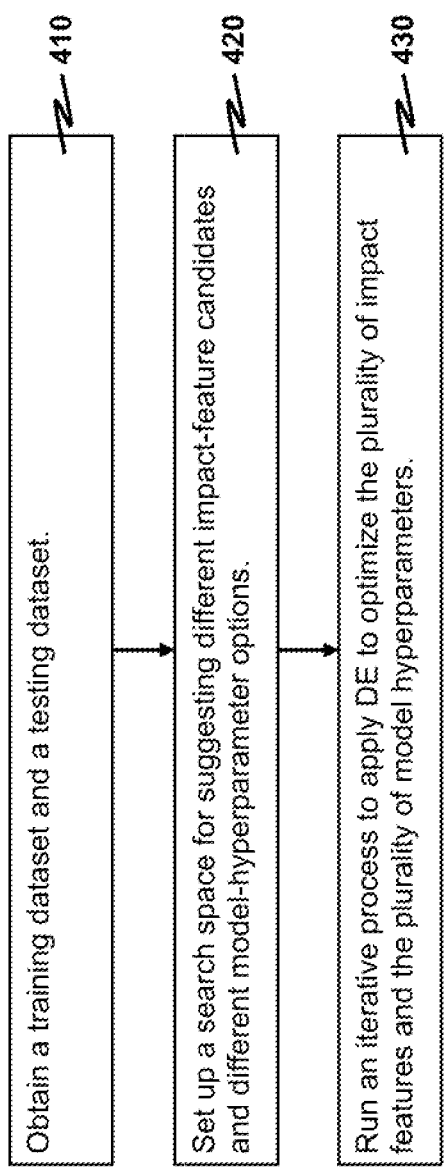
FIG. 4 depicts a flowchart showing an exemplary procedure of learning a plurality of impact features, a plurality of model hyperparameters and a plurality of ANN model parameters by a DE technique as used in the disclosed method.

FIG. 4 depicts a flowchart showing an exemplary procedure of the step 220. The step 220 comprises steps 410, 420 and 430.

In the step 410, training dataset and testing dataset are obtained. The training dataset is used for training the ANN 115 while the testing dataset is used for verifying the ANN 115 after the ANN 115 is trained. Typically, each of the two datasets is obtained from historical data of water quality measures and meaningful features.

In the step 420, a search space for suggesting different impact-feature candidates and different model-hyperparameter options is set up. As mentioned above, the individual impact feature is selected from the plurality of impact-feature candidates. Similarly, an individual model hyperparameter is selected from a plurality of model-hyperparameter options. The search space is set up such that the plurality of impact-feature candidates and the plurality of model-hyperparameter options are obtainable from the search space.

In certain embodiments, the search space is organized as plural groups of elementary features. Respective elementary features in an individual elementary-feature group are of a same type in some meaningful sense. Combining elementary features selected from different elementary-feature groups yields one impact-feature candidate or model-hyperparameter option. An illustrative example of the search space is provided in Table 2, where the search space is organized with nine elementary-feature groups.

TABLE 2

| Group | Type | Elementary feature | Remark |
|---|---|---|---|
| 1 | Observation variable (static) | Water-source location | |
| 2 | Observation variable (time-varying) | Climatic indicators (rainfall, temperature, etc.), chemical indicators (nitrogen content, phosphor content, etc.), biological indicators (bacteria concentration, etc.) | |
| 3 | Sampling | No downsampling (keeping all raw data), sampled hourly, sampled daily, etc. | (A) |
| 4 | Periodicity | Periodic pattern of period less than one hour, periodic pattern of period less than one day, etc. | (A) |
| 5 | DC | DC under DC threshold of 1%, DC under DC threshold of 5%, etc. | (A) |
| 6 | Observation window | Window of size A, window of size B, etc. | (A) |
| 7 | ANN type | MLP, LSTM, GRU, etc. | |
| 8 | ANN size | Number of ANN layers | (B) |
| 9 | Activation function | Activation function A, activation function B, etc. | (B) |

Remark:
(A) applied to Group 2;
(B) applied to Group 7.

In the step 430, an iterative process for optimizing the plurality of impact features and the plurality of model hyperparameters according to DE is performed. The iterative process is exemplarily illustrated by elaborating the SODE controller 120 of the framework 100. As mentioned above, the SODE controller 120 is used for learning the plurality of impact features 122 and the plurality of model hyperparameters 124 based on a DE technique.

Figure 5:
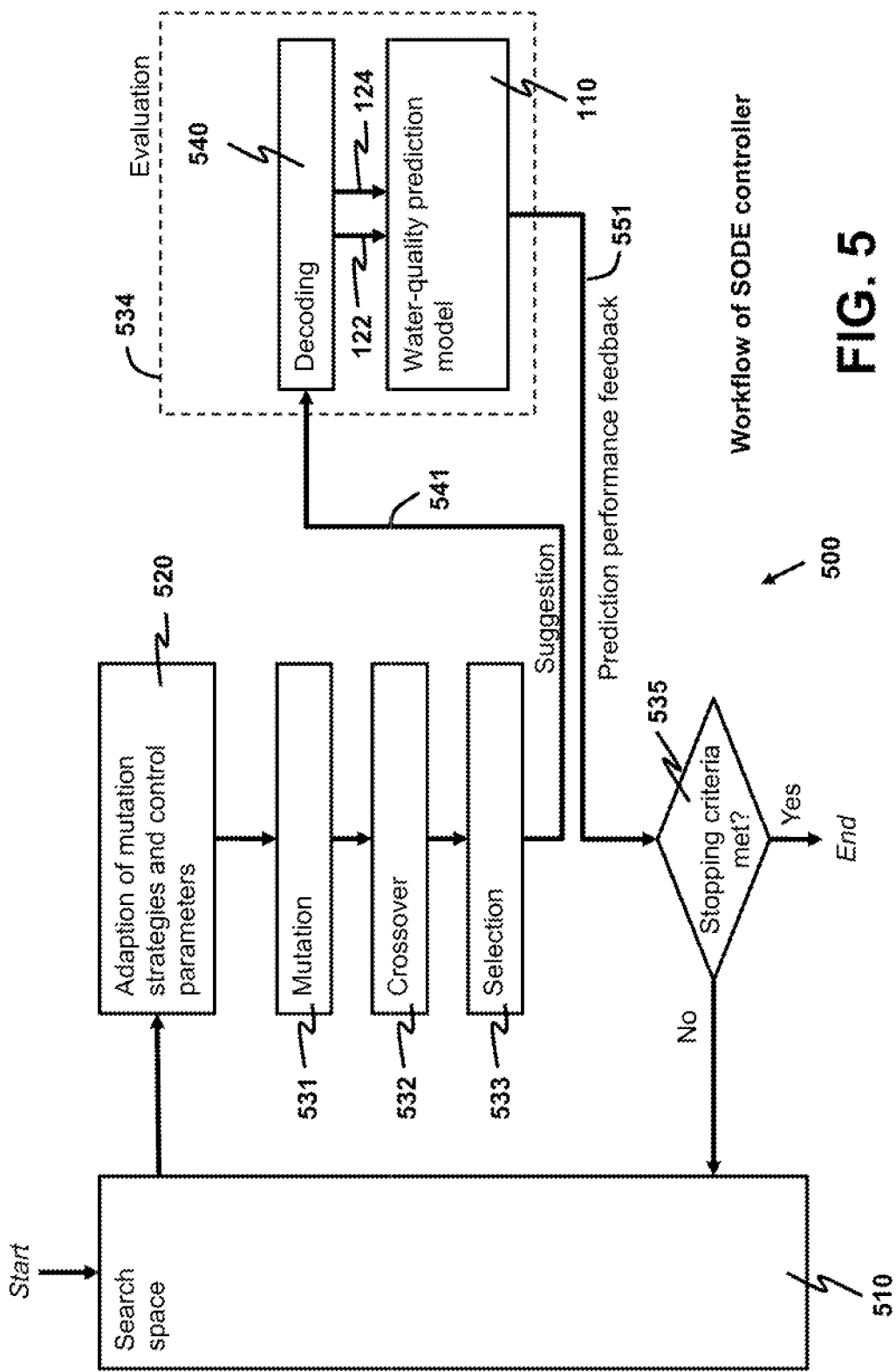
FIG. 5 depicts a workflow diagram of the SODE controller, showing an iterative process performed by the SODE controller.

FIG. 5 depicts a workflow diagram of the SODE controller 120, showing an iterative process 500 performed by the SODE controller 120. Denote an initial iteration as the first iteration (a starting iteration) before which no iteration has been performed in the iterative process 500.

In an individual iteration of the iterative process 500, a suggestion 541 on both of the plurality of impact features 122 and the plurality of model hyperparameters 124 is generated. That is, the suggestion 541 contains a first suggestion on the plurality of impact features 122 and a second suggestion on the plurality of model hyperparameters 124. If the individual iteration is the initial iteration, the suggestion 541 is initialized with a preset suggestion or is randomly generated in the search space (referenced as 510). If the individual iteration is not the initial iteration such that one or more past iterations have been performed, the suggestion 541 is generated by performing DE-based operations of mutation 531, crossover 532 and selection 533 in the search space 510 after mutation strategies and control parameters 520 of the three DE-based operations 531-533 are adapted according to historical performance of water-quality prediction due to suggestions made in the one or more past iterations. Those skilled in the art will appreciate that the three DE-based operations 531-533 can be formulated according to any DE technique known in the art, e.g., in the disclosure of R. STORN and K. PRICE.

The suggestion 541 is then evaluated 534 by assessing the water-quality prediction performance based on using the suggestion 541 in configuring the water-quality prediction model 110, as explained as follows.

After the suggestion 541 is generated in the individual iteration, the architecture and input-output relationship of the ANN 115 are configured according to the suggestion 541. Thereafter, the plurality of ANN model parameters 126 is learnt by training the ANN 115 according to data in the training dataset. As a result, the ANN 115 is trained. A prediction accuracy of the trained ANN 115 is verified according to data in the testing dataset, thereby yielding a prediction-performance value as a feedback 551 from the water-quality prediction model 110 to the SODE controller 120.

If the prediction-performance value converges (by comparing this value with previous prediction-performance values obtained in the one or more past iterations) or a predefined stopping criterion is met (e.g., reaching a predetermined maximum number of allowable iterations), then the iterative process 500 is terminated such that the trained ANN 115 as obtained in the individual iteration is usable for inference (step 535). If not, proceed to execute a next iteration (the step 535).

In the individual iteration, it is possible that the generated suggestion 541 is required to be decoded into the plurality of impact features 122 and the plurality of model hyperparameters 124 by a decoding algorithm 540 such that the plurality of impact features 122 and the plurality of model hyperparameters 124 as decoded are presented in a format interpretable by the ANN 115 (or the water-quality prediction model 110) to thereby allow the ANN 115 (or the water-quality prediction model 110) to be correctly configured. The need for the decoding algorithm 540 is explained as follows. As the impact factors in water-quality prediction have different definition ranges and representation formats, these impact factors are required to be processed and optimized by different ways. Yet most existing meta-heuristic algorithms are designed for one of data types like real number or binary data. Compared to these existing algorithms, the decoding algorithm 540 used by the SODE controller 120 can optimize features in multiple data types at the same time. The optimized SODE solution can be transformed to the problem solution in terms of corresponding transformation rules, and then send to the prediction model 110 for evaluation.

The transformation rules as disclosed herein are given in Table 3. In Table 3, $x_i$ stands for a value in the suggestion 541, and $x_i'$ stands for a corresponding value in the plurality of impact features 122 or the plurality of model hyperparameters 124 as decoded. In Table 3, furthermore, it is considered that $x_i \in [lb_i, ub_i]$, $x_i' \in [lb_i', ub_i']$, $i=1, 2, \ldots, D$, and it is assumed that $lb_i=-1$, $ub_i=1$, $lb_i'=0$, $ub_i'=16$ as examples for illustration. Table 4 lists ranges of SODE solutions ($x_i$) against corresponding ranges of problem solutions ($x_i'$) for different data types.

TABLE 3

| Data Type | Transformation Rules ($x_i \to x_i'$) |
|---|---|
| Binary data | $x_i' = \begin{cases} 0, & \text{if } x_i < lb_i + \dfrac{ub_i - lb_i}{2} \\ 1, & \text{otherwise} \end{cases}$ |
| Category data | One-hot decoding |
| Integer data | $x_i' = \text{Round}\left(\dfrac{x_i - lb_i}{ub_i - lb_i} \times (ub_i' - lb_i') + lb_i'\right)$ |
| Real number data | $x_i' = \dfrac{x_i - lb_i}{ub_i - lb_i} \times (ub_i' - lb_i') + lb_i'$ |

TABLE 4

| Data Type | SODE solution ($x_i$) | Problem solution ($x_i'$) |
|---|---|---|
| Binary data | [−0.5, 0.7] | [0, 1] |
| Category data | ar gmax [0.1, 0.3, 0.9, 0.7] | [2] |
| Integer data | [0.8, −0.6] | [14, 3] |
| Real number data | [0.8, −0.6] | [14.4, 3.2] |

In certain embodiments of the disclosed method, the decoding algorithm 540 is configured with a plurality of transformation rules respectively used for processing data of a plurality of data types. The plurality of data types includes binary data type, category data type, integer data type and real number data type. The plurality of transformation rules may follow the transformation rules of Table 3.

In the individual iteration, as mentioned above, the mutation strategies and control parameters 520 are required to be adapted according to the historical performance of water-quality prediction due to suggestions made in the one or more past iterations. To enhance the search efficiency at different problems and search stages, a flexible search strategy and control parameters instead of fixed values can better adapt to search environments to balance exploration and exploitation. Most of the adaptive methods in meta-heuristic algorithms are complicated so that much more processing time is required. Thus, the disclosed method adopts a simple yet efficient adaptive mechanism for selecting mutation strategies and control parameters 520 in terms of the weighted historical performance.

In certain embodiments of the disclosed method, the mutation strategies and control parameters 520 are adapted by a mutation-strategy adaption mechanism and a control-parameter adaption mechanism, respectively, for enhancing an efficiency in searching for the suggestion 541 across different situations of water-quality prediction. In the mutation-strategy adaption mechanism, the mutation strategies are adapted by adjusting selection probabilities of each mutation strategy according to historical ranking-based performance among the mutation strategies. In the control-parameter adaption mechanism, the control parameters are adapted by respectively adjusting the control parameters to weighted successful control parameters obtained in the past iterations.

Figure 6:
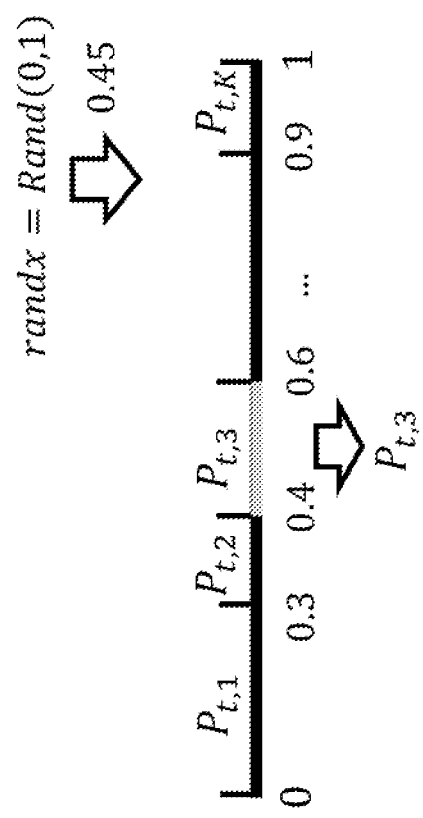
FIG. 6 pictorially illustrates a roulette wheel selection procedure for selecting a mutation strategy in the DE technique.

In certain embodiments, the mutation-strategy adaption mechanism is given as follows. Let $P_{t,k}'$ and $P_{t,k}$ be the unnormalized probability and the normalized probability, respectively, of the kth strategy at the tth iteration. The two probabilities are computed by $$P_{t,k}' = \frac{\sum_{i=1, i \in k}^{M_{t,k}} (N - \text{rank}_{t,i} + 1)}{\sum_{j=1}^{K} \sum_{i=1, i \in j}^{M_{t,j}} (N - \text{rank}_{t,i} + 1)} \tag{1}$$

and $$P_{t,k} = \frac{\sum_{r=1}^{T} w_{t=r,k} P_{t-r,k}'}{\sum_{j=1}^{K} \sum_{r=1}^{T} w_{t-r,j} P_{t-r,j}'}, \tag{2}$$

where N is the number of individuals, $\text{rank}_{t,j}$ is the ranking of ith individual in term of the fitness value at the tth iteration, and $w_{t-r,k}$ denotes the weights of the kth strategy at the (t−r)th iteration. The normalized probability $P_{t,k}$ is used as the selection probability of the kth strategy at the tth iteration. A roulette wheel selection procedure is used to determine which one of the normalized probabilities is selected at the tth iteration. FIG. 6 pictorially illustrates the roulette wheel selection procedure. The normalized probabilities for all the K strategies, given by $P_{t,1}, P_{t,2}, \ldots, P_{t,K}$, are respectively represented by line segments on a line, where the line segment for the kth strategy has a length determined according to $P_{t,k}$. In this fashion, the partition of the line into K line segments resemble a cumulative probability distribution for the K strategies. A random number between 0 and 1 is generated. By projecting the generated random number onto the line, which one of the K strategies is selected in the tth iteration is thereby identified.

In certain embodiments, the control-parameter adaption mechanism is given as follows. The control parameters of interest to DE are the crossover rate and the scaling factor, given by $$CR_{t,i} = N(S_{t,CR}, 0.1^2) \tag{3}$$

and $$F_{t,i} = C(S_{t,F}, 0.1^2) \tag{4}$$

where $S_{t-1,k}$ is the set of enhanced individuals of kth strategy at the (t−1)th iteration, $N(S_{t,CR}, 0.1^2)$ is the generator following the Normal distribution with the mean at $S_{t,CR}$, $C(S_{t,F}, 0.1^2)$ is the generator following the Cauchy distribution with the mean at $S_{t,F}$, $CR_{t,i}$ is the crossover rate of ith individual, and $F_{t,i}$ is the scaling factor of ith individual. In particular, $S_{t,CR}$ and $S_{t,F}$ are given by $$S_{t,CR} = \sum_{j=1}^{K} \frac{P_{t-1,j}}{M_k} \sum_{i=1, i \in S_{t-1,k}}^{M_k} CR_{t-1,i} \tag{5}$$

and $$S_{t,F} = \sum_{j=1}^{K} \frac{P_{t-1,j}}{M_k} \sum_{i=1, i \in S_{t-1,k}}^{M_k} F_{t-1,i}, \tag{6}$$

respectively.

Other implementation details of the disclosed method are elaborated as follows.

In certain embodiments, the plurality of model hyperparameters 124 is arranged to provide information at least on type and size of the ANN 115 to the ANN 115. The plurality of model-hyperparameter options, from which the plurality of model hyperparameters 124 is selected, includes different combinations of the ANN type and the ANN size. The ANN type used in generating the different combinations may be selected from a MLP, a LSTM and a GRU.

The ANN 115 may be deemed as a multi-input single-output system in that plural feature-data sequences associated with the plurality of impact features 122 form multiple inputs to the ANN 115 and the ANN 115 generates the predicted water-quality data 170, which form a single output. Preferably, the ANN 115 is a modular neural network for more efficiently handle processing the impact-feature data 165 than using a monolithic neural network.

Figure 7:
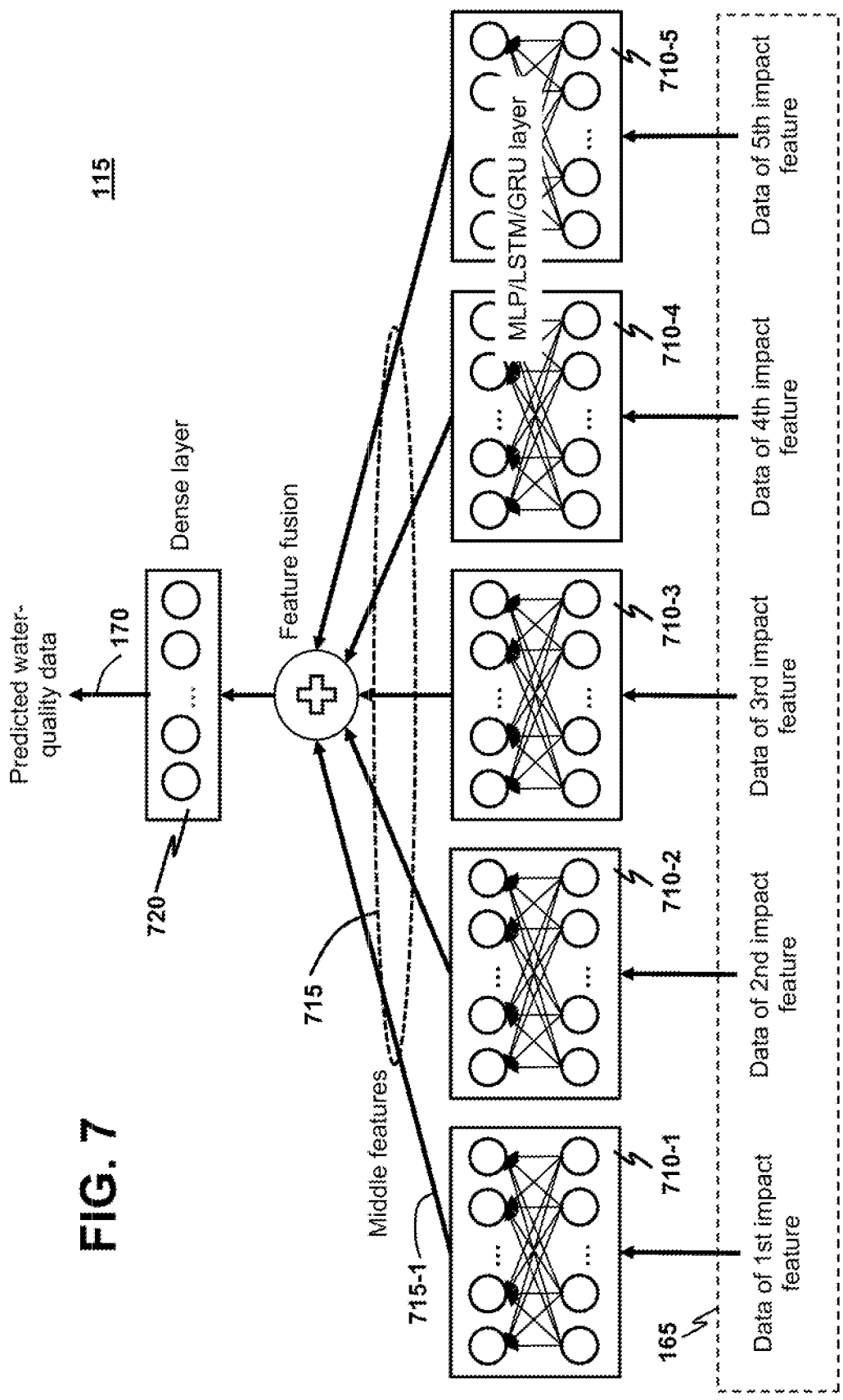
FIG. 7 depicts a realization of the ANN by using a modular neural network.

FIG. 7 depicts a realization of the ANN 115 by using a modular neural network structure. The ANN 155 comprises a plurality of learning submodules 710-1:5 for processing the feature data 165 associated with the plurality of impact features 122. An individual learning submodule is realized as a standalone neural network for processing feature data associated with a corresponding impact feature selected from the plurality of impact features 122 to thereby yield feature data of a middle feature (e.g., middle feature 715-1). A plurality of middle features 715 is formed. The ANN 155 further comprises a dense layer 720 for fusing feature data of respective middle features 715 to generate the predicted water-quality data 170. The dense layer 720 is a layer that is deeply connected with its preceding layer. That is, neurons of the dense layer 720 are connected to every neuron of its preceding layer.

Optionally, each learning submodule in the plurality of learning submodules 710-1:5 is realized by a MLP, a LSTM or a GRU.

As mentioned above, the self-adaptive water quality prediction framework 100 is an implementation of a certain embodiment of the disclosed method. For realizing the framework 100, the step 210, apart from setting up the ANN 115, further includes setting up the data augmentation module 112 and the SODE controller 120. Since the disclosed method is a computer-implemented method, setting up the SODE controller 120 means providing a software realization of the SODE controller 120 with desired properties as taught herein in one or more computers or in any computing device. The meaning of setting up the data augmentation module 112 is similar. In addition, the SODE controller 120 is further arranged to perform the iterative process 500, and to perform the following actions during execution of the individual iteration of the iterative process 500. First, the SODE controller 120 sends the plurality of model hyperparameters 124 and the plurality of impact features 122 as decoded (i.e. after decoded by the decoding algorithm 540) to the ANN 115 and the data augmentation module 112, respectively, so as to configure the ANN architecture and to inform the data augmentation module 112 to calculate the feature data 165 associated with the plurality of impact features 122. Second, the SODE controller 120 trains the ANN 115 by commanding the data augmentation module 112 to process the observation data recorded in the training dataset, and by commanding the ANN 115 to send the predicted water-quality data 170 as obtained to the SODE controller 120. Third, the SODE controller 120 verifies the prediction accuracy of the trained ANN 115 by commanding the data augmentation model 112 to process the observation data recorded in the testing dataset, and by commanding the ANN 115 to send the predicted water-quality data 170 as obtained to the SODE controller 120.

To evaluate the disclosed method, the proposed self-adaptive water quality prediction framework 100 is compared with other popular water-quality prediction frameworks. Experiments on water-quality prediction were conducted.

A water-quality database records hour-based pH values between October 2018 and October 2021 from an observation station in Hong Kong. The training dataset is formed with database records taken from October 2018 to November 2020 while the testing dataset has database records taken from December 2020 to October 2021. The experiments evaluated performances of water-quality prediction frameworks on the pH value prediction in 1-hour/12-hour/24-hour predicting intervals.

For fair comparison, three popular backbones including MLP, LSTM and GRU were applied to construct baseline algorithms and the proposed framework 100. MSE values as experimentally obtained were recorded and compared, where the MSE was computed by $$MSE = \frac{1}{n}\sum_{i=1}^{n}(y_{pred}^i - y_{true}^i)^2. \qquad (7)$$

where n is the number of instances of observation in the experiment, $y_{true}^i$ is an actual water-quality data obtained in the ith instance of observation, and $y_{pred}^i$ is a predicted water-quality data computed in the ith instance of observation.

Table 5 lists MSE values for a baseline framework and the self-adaptive water quality prediction framework 100 (short-handed as "self-adaptive framework") under predicting intervals of: (a) 1 hr; (b) 12 hr; and (c) 24 hr.

TABLE 5

(a): 1-hour predicting interval.

| Backbone | MLP | LSTM | GRU |
| --- | --- | --- | --- |
| Baseline framework | 0.0094 | 0.0087 | 0.0086 |
| Self-adaptive framework | 0.0084 | 0.0083 | 0.0085 |

(b): 12-hour predicting interval.

| Backbone | MLP | LSTM | GRU |
| --- | --- | --- | --- |
| Baseline framework | 0.0607 | 0.0605 | 0.0605 |
| Self-adaptive framework | 0.0604 | 0.0605 | 0.0610 |

(c): 24-hour predicting interval.

| Backbone | MLP | LSTM | GRU |
| --- | --- | --- | --- |
| Baseline framework | 0.0613 | 0.0610 | 0.0611 |
| Self-adaptive framework | 0.0611 | 0.0609 | 0.0612 |

From the experimental data shown in Table 5, it is observed that the proposed self-adaptive water quality prediction framework 100 achieves a better water-quality prediction performance than the baseline framework does in most cases.

To demonstrate the superior performance of the proposed framework 100 over the baseline framework in the presence of extreme/unexpected events, FIG. 8 plots the actually-measured pH values (marked as "True" in FIG. 8) and the predicted pH values (marked as "Predict" in FIG. 8) over time as obtained in the experiment, where in subplot (a) 810 and subplot (b) 820, the predicted pH values were computed by the proposed framework 100 and by the baseline framework, respectively. From the two subplots, it is observed that the prediction accuracy achieved by the proposed framework 100 is notably better than that achieved by the baseline framework at time instants where extreme/unexpected events 830 occur.

The disclosed method, being a computer-implemented method, may be implemented on one or more computing devices with appropriate programming. An individual computing device may be a general-purpose computer, a special-purpose computer such as the one implemented with artificial intelligence processor(s), a desktop computer, a physical computing server, a distributed computing server in a computing cloud, or a mobile computing device such as a notebook computer, a tablet computer and a smartphone.

In the present disclosure, an entirety of embodiments of the disclosed method includes a first set of embodiments each comprising limitations as taught herein for solving the first technical problem, a second set of embodiments each comprising limitations as taught herein for solving the second technical problem, and a third set of embodiments each comprising limitations taught herein and collectively used for solving the first and second technical problems. It is intended that the disclosed method encompasses all embodiments including the first, second and third sets of embodiments and equivalents thereof.

The present disclosure may be embodied in other specific forms without departing from the spirit or essential characteristics thereof. The present embodiment is therefore to be considered in all respects as illustrative and not restrictive. The scope of the invention is indicated by the appended claims rather than by the foregoing description, and all changes that come within the meaning and range of equivalency of the claims are therefore intended to be embraced therein.

What is claimed is:

1. A computer-implemented method for predicting water quality from observation data associated with a plurality of raw features relevant to water-quality prediction to thereby generate predicted water-quality data, the method comprising:

setting up an artificial neural network (ANN) for computing the predicted water-quality data from feature data associated with a plurality of impact features, the feature data associated with the plurality of impact features being computed from the observation data, wherein the plurality of impact features is learnable, an architecture of the ANN is configurable according to a plurality of model hyperparameters, and the ANN has a plurality of ANN model parameters for configuring an input-output relationship of the ANN; and learning the plurality of impact features, the plurality of model hyperparameters and the plurality of ANN model parameters, wherein in learning the plurality of impact features, an individual impact feature is selected from a plurality of impact-feature candidates comprising a plurality of directional change-(DC-)based features, wherein an individual DC-based feature is associated with a corresponding raw feature and is used to indicate occurrence of any DC event in the corresponding raw feature, an inclusion of the individual DC-based feature in the plurality of impact-feature candidates enhancing the ANN's ability of capturing possible significant change patterns of water quality due to extreme or unexpected events.

2. The method of claim 1, wherein:

the individual DC-based feature is further associated with a DC threshold for controlling detection of any DC event in the corresponding raw feature; and plural respective DC-based features associated with a same corresponding raw feature are associated with different DC thresholds for enabling the ANN to more effectively learn to distinguish extreme or unexpected events of different degrees of severity.

3. The method of claim 1, wherein:

the plurality of impact-feature candidates further comprises a plurality of downsampled raw features; and the individual DC-based feature is further associated with a corresponding downsampled raw feature, wherein feature data associated with the corresponding downsampled raw feature are obtained by downsampling respective observation data associated with the corresponding raw feature.

4. The method of claim 3, wherein the corresponding raw feature is excluded from the plurality of impact-feature candidates such that an inclusion of the individual DC-based feature and the corresponding downsampled raw feature into the plurality of impact-feature candidates enhances the ANN's ability of capturing possible significant change patterns of water quality due to extreme or unexpected events while avoiding the ANN from directly processing feature data associated with the corresponding raw feature.

5. The method of claim 1, wherein the plurality of impact features and the plurality of model hyperparameters are learnt by differential evolution (DE) for maximizing a water-quality prediction performance achieved by the ANN, thereby enabling the ANN architecture and the plurality of impact features to be automatically optimized without a need for manual adjustment by domain experts in applying the ANN to different situations of water-quality prediction.

6. The method of claim 5, wherein the learning of the plurality of impact features, the plurality of model hyperparameters and the plurality of ANN model parameters comprises:
obtaining a training dataset for training the ANN, and a testing dataset for verifying the trained ANN;
setting up a search space for suggesting different impact-feature candidates and different model-hyperparameter options such that the plurality of impact-feature candidates and a plurality of model-hyperparameter options are obtainable from the search space, wherein the plurality of model hyperparameters is selected from the plurality of model-hyperparameter options; and
performing an iterative process, wherein an individual iteration of the iterative process comprises:
generating a suggestion on both of the plurality of impact features and the plurality of model hyperparameters, wherein if said individual iteration is an initial iteration, the suggestion is initialized with a preset suggestion or is randomly generated in the search space, else the suggestion is generated by performing DE-based operations of mutation, crossover and selection in the search space after mutation strategies and control parameters of the three DE-based operations are adapted according to historical performance of water-quality prediction due to suggestions made in past iterations;
configuring the architecture and input-output relationship of the ANN according to the suggestion;
after the architecture and input-output relationship of the ANN are configured, learning the plurality of ANN model parameters by training the ANN according to data in the training dataset, whereby the trained ANN is obtained;
verifying a prediction accuracy of the trained ANN according to data in the testing dataset to thereby yield a prediction-performance value; and
if the prediction-performance value converges or a predefined stopping criterion is met, then terminating the iterative process such that the trained ANN as obtained in said individual iteration is usable for inference, else proceeding to execute a next iteration.

7. The method of claim 6, wherein the mutation strategies and control parameters are adapted by a mutation-strategy adaption mechanism and a control-parameter adaption mechanism, respectively, for enhancing an efficiency in searching for the suggestion across different situations of water-quality prediction, wherein:
in the mutation-strategy adaption mechanism, the mutation strategies are adapted by adjusting selection probabilities of each mutation strategy according to historical ranking-based performance among the mutation strategies; and
in the control-parameter adaption mechanism, the control parameters are adapted by respectively adjusting the control parameters to weighted successful control parameters obtained in the past iterations.

8. The method of claim 6, wherein said individual iteration of the iterative process further comprises:
decoding the generated suggestion into the plurality of impact features and the plurality of model hyperparameters by a decoding algorithm such that the plurality of impact features and the plurality of model hyperparameters as decoded are interpretable by the ANN, wherein the decoding algorithm is configured with a plurality of transformation rules respectively used for processing data of a plurality of data types, and wherein the plurality of data types includes binary data type, category data type, integer data type and real number data type.

9. The method of claim 8 further comprising:
setting up a data augmentation module for computing the feature data associated with the plurality of impact features from the observation data, whereby a water-quality prediction model for computing the predicted water-quality data from the observation data is formed by a cascade of the data augmentation module and the ANN; and
setting up a self-adaptive optimization differential evolution (SODE) controller for learning the plurality of impact features and the plurality of model hyperparameters, wherein the SODE controller is communicable with the water-quality prediction model, and is arranged to:
perform the iterative process;
during execution of said individual iteration, send the plurality of model hyperparameters and the plurality of impact features as decoded to the ANN and the data augmentation module, respectively, so as to configure the ANN architecture and to inform the data augmentation module to calculate the feature data associated with the plurality of impact features;
during execution of said individual iteration, train the ANN by commanding the data augmentation module to process the observation data recorded in the training dataset, and by commanding the ANN to send the predicted water-quality data as obtained to the SODE controller; and
during execution of said individual iteration, verify the prediction accuracy of the trained ANN by commanding the data augmentation model to process the observation data recorded in the testing dataset, and by commanding the ANN to send the predicted water-quality data as obtained to the SODE controller.

10. The method of claim 1, wherein the plurality of model hyperparameters is arranged to provide information at least on type and size of the ANN to the ANN, and the plurality of model-hyperparameter options includes different combinations of the ANN type and the ANN size.

11. The method of claim 10, wherein the ANN type used in generating the different combinations is selected from a multi-layer perceptron (MLP), a long short-term memory (LSTM) and a gated recurrent unit (GRU).

12. The method of claim 1, wherein the ANN is a modular neural network comprising:
a plurality of learning submodules for processing the feature data associated with the plurality of impact features, wherein an individual learning submodule is realized as a standalone neural network for processing feature data associated with a corresponding impact feature selected from the plurality of impact features to thereby yield feature data of a middle feature; and
a dense layer for fusing feature data of respective middle features to generate the predicted water-quality data.

13. The method of claim 12, wherein the individual learning submodule is realized by a multi-layer perceptron (MLP), a long short-term memory (LSTM) or a gated recurrent unit (GRU).

14. The method of claim 1 further comprising:
after the architecture and input-output relationship of the ANN are configured by the learnt plurality of model hyperparameters and the learnt plurality of the ANN model parameters, respectively, inferring the predicted water-quality data from the observation data by computing the feature data associated with the learnt plurality of impact features from the observation data and then using the ANN to compute the predicted water-quality data from the computed feature data associated with the learnt plurality of impact features.

15. A computer-implemented method for predicting water quality from observation data associated with a plurality of raw features relevant to water-quality prediction to thereby generate predicted water-quality data, the method comprising:
setting up an artificial neural network (ANN) for computing the predicted water-quality data from feature data associated with a plurality of impact features, the feature data associated with the plurality of impact features being computed from the observation data, wherein the plurality of impact features is learnable, an architecture of the ANN is configurable according to a plurality of model hyperparameters, and the ANN has a plurality of ANN model parameters for configuring an input-output relationship of the ANN; and
learning the plurality of impact features, the plurality of model hyperparameters and the plurality of ANN model parameters, wherein the plurality of impact features and the plurality of model hyperparameters are learnt by differential evolution (DE) for maximizing a water-quality prediction performance achieved by the ANN, thereby enabling the ANN architecture and the plurality of impact features to be automatically optimized without a need for manual adjustment by domain experts in applying the ANN to different situations of water-quality prediction.

16. The method of claim 15, wherein the learning of the plurality of impact features, the plurality of model hyperparameters and the plurality of ANN model parameters comprises:
obtaining a training dataset for training the ANN, and a testing dataset for verifying the trained ANN;
setting up a search space for suggesting different impact-feature candidates and different model-hyperparameter options such that the plurality of impact-feature candidates and a plurality of model-hyperparameter options are obtainable from the search space, wherein the plurality of model hyperparameters is selected from the plurality of model-hyperparameter options; and
performing an iterative process, wherein an individual iteration of the iterative process comprises:
generating a suggestion on both of the plurality of impact features and the plurality of model hyperparameters, wherein if said individual iteration is an initial iteration, the suggestion is initialized with a preset suggestion or is randomly generated in the search space, else the suggestion is generated by performing DE-based operations of mutation, crossover and selection in the search space after mutation strategies and control parameters of the three DE-based operations are adapted according to historical performance of water-quality prediction due to suggestions made in past iterations;
configuring the architecture and input-output relationship of the ANN according to the suggestion;
after the architecture and input-output relationship of the ANN are configured, learning the plurality of ANN model parameters by training the ANN according to data in the training dataset, whereby the trained ANN is obtained;
verifying a prediction accuracy of the trained ANN according to data in the testing dataset to thereby yield a prediction-performance value; and
if the prediction-performance value converges or a predefined stopping criterion is met, then terminating the iterative process such that the trained ANN as obtained in said individual iteration is usable for inference, else proceeding to execute a next iteration.

17. The method of claim 16, wherein the mutation strategies and control parameters are adapted by a mutation-strategy adaption mechanism and a control-parameter adaption mechanism, respectively, for enhancing an efficiency in searching for the suggestion across different situations of water-quality prediction, wherein:
in the mutation-strategy adaption mechanism, the mutation strategies are adapted by adjusting selection probabilities of each mutation strategy according to historical ranking-based performance among the mutation strategies; and
in the control-parameter adaption mechanism, the control parameters are adapted by respectively adjusting the control parameters to weighted successful control parameters obtained in the past iterations.

18. The method of claim 16, wherein said individual iteration of the iterative process further comprises:
decoding the generated suggestion into the plurality of impact features and the plurality of model hyperparameters by a decoding algorithm such that the plurality of impact features and the plurality of model hyperparameters as decoded are interpretable by the ANN, wherein the decoding algorithm is configured with a plurality of transformation rules respectively used for processing data of a plurality of data types, and wherein the plurality of data types includes binary data type, category data type, integer data type and real number data type.

19. The method of claim 18 further comprising:
setting up a data augmentation module for computing the feature data associated with the plurality of impact features from the observation data, whereby a water-quality prediction model for computing the predicted water-quality data from the observation data is formed by a cascade of the data augmentation module and the ANN; and
setting up a self-adaptive optimization differential evolution (SODE) controller for learning the plurality of impact features and the plurality of model hyperparameters, wherein the SODE controller is communicable with the water-quality prediction model, and is arranged to:

perform the iterative process;

during execution of said individual iteration, send the plurality of model hyperparameters and the plurality of impact features as decoded to the ANN and the data augmentation module, respectively, so as to configure the ANN architecture and to inform the data augmentation module to calculate the feature data associated with the plurality of impact features;

during execution of said individual iteration, train the ANN by commanding the data augmentation module to process the observation data recorded in the training dataset, and by commanding the ANN to send the predicted water-quality data as obtained to the SODE controller; and during execution of said individual iteration, verify the prediction accuracy of the trained ANN by commanding the data augmentation model to process the observation data recorded in the testing dataset, and by commanding the ANN to send the predicted water-quality data as obtained to the SODE controller.

20. The method of claim 15 further comprising:

after the architecture and input-output relationship of the ANN are configured by the learnt plurality of model hyperparameters and the learnt plurality of the ANN model parameters, respectively, inferring the predicted water-quality data from the observation data by computing the feature data associated with the learnt plurality of impact features from the observation data and then using the ANN to compute the predicted water-quality data from the computed feature data associated with the learnt plurality of impact features.

* * * * *